United States Patent [19]
Boisclair et al.

[11] Patent Number: 5,619,747
[45] Date of Patent: Apr. 15, 1997

[54] PROTECTIVE BRACE FOR FIGURE SKATERS

[76] Inventors: Carole Boisclair; Marcel Tousignant, both of 931 Avenue des Cèdres, Shawinigan, Qc, Canada, G9N 1P4

[21] Appl. No.: 544,876

[22] Filed: Oct. 18, 1995

[51] Int. Cl.$^6$ ............................. A41D 13/00; A61F 5/02
[52] U.S. Cl. ........................... 2/465; 2/44; 2/467; 602/5
[58] Field of Search .................. 2/2, 44, 45, 92; 602/18, 19, 20, 23, 5; 128/869, 870, 873, 874, 875

[56] References Cited

U.S. PATENT DOCUMENTS

| | | |
|---|---|---|
| 4,026,547 | 5/1977 | Silverstople et al. ............ 2/44 |
| 4,151,613 | 5/1979 | Rhee . |
| 4,680,812 | 7/1987 | Weigl . |
| 4,761,834 | 8/1988 | Kolb . |
| 4,807,301 | 2/1989 | Ferber . |
| 4,993,076 | 2/1991 | Dierickx . |
| 5,052,052 | 10/1991 | Gilford . |
| 5,361,410 | 11/1994 | Sigl ............................. 2/267 |
| 5,362,304 | 11/1994 | Varn ............................ 2/44 |

FOREIGN PATENT DOCUMENTS

| | | |
|---|---|---|
| 1046201 | 1/1979 | Canada . |
| 1131852 | 9/1982 | Canada . |
| 1321855 | 9/1993 | Canada . |

*Primary Examiner*—C. D. Crowder
*Assistant Examiner*—Larry D. Worrell, Jr.
*Attorney, Agent, or Firm*—François Martineau

[57] ABSTRACT

The protective brace is worn by a figure skater to prevent impact borne bone bruising resulting from one or more falls of the skater on the ice. The brace has a semi-rigid, resilient plastic shell. The latter has a generally rectangular web defining a longitudinal axis and having two downwardly oriented, wide, curved extensions at the respective extremities of the longitudinal axis. The shell has a lower and an upper tongue integrally and orthogonally extending from the middle of the web respectively downwardly and upwardly. The shell is molded to fit a particular skater, the web resting on the lombo-sacral area of the back of the skater and molded so as to position the longitudinal axis partially around the hips, the two curved extensions projecting downwardly from the hips over the thighs, the lower tongue straddling over the coccygeal section of the spine and the upper tongue extending over the lombo-thoracic section of the spine. The brace further comprises ten straps that are attached to the shell and that are destined to steadfastly and removably secure the shell adjustably to the body of the skater. The shell is of such a shape that it does not surround significantly any body articulation, so as to allow a relatively good freedom of movement to the skater wearing the brace. Indeed, the only part of the brace that surrounds the articulations is the light, uncumbersome straps.

10 Claims, 2 Drawing Sheets

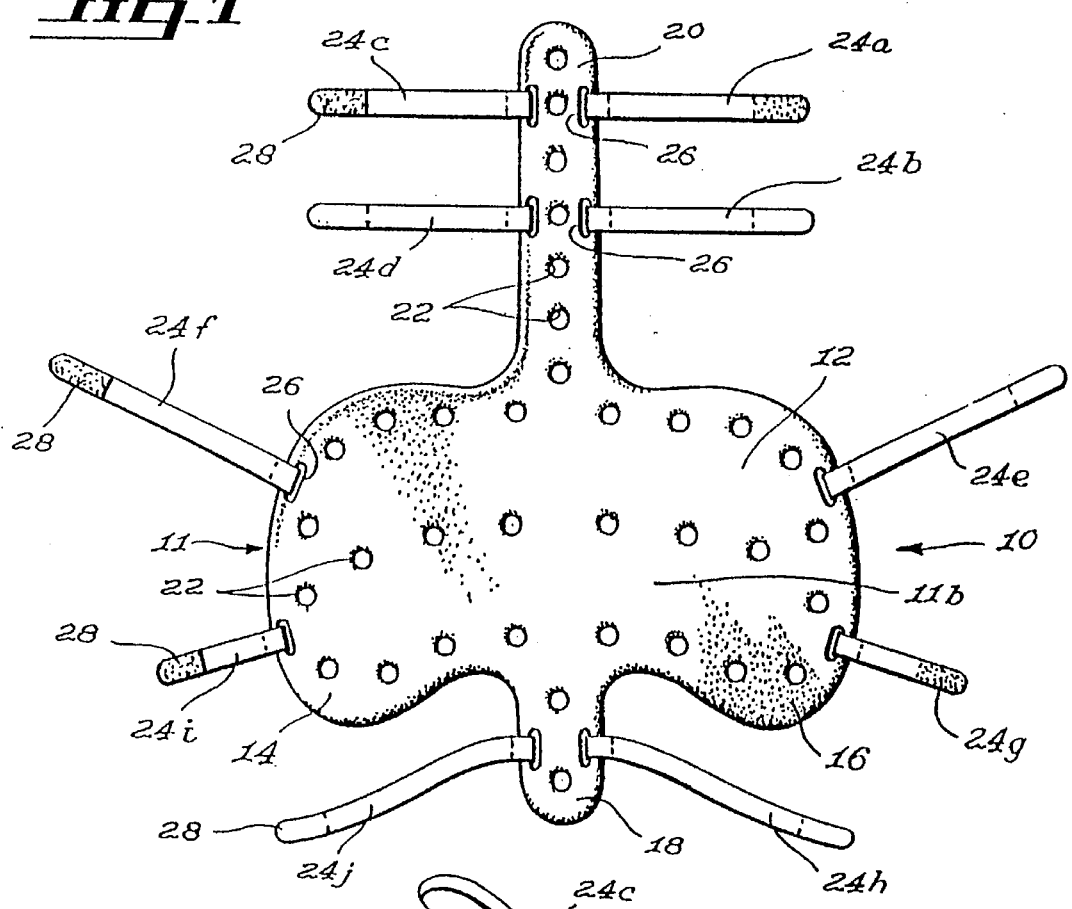
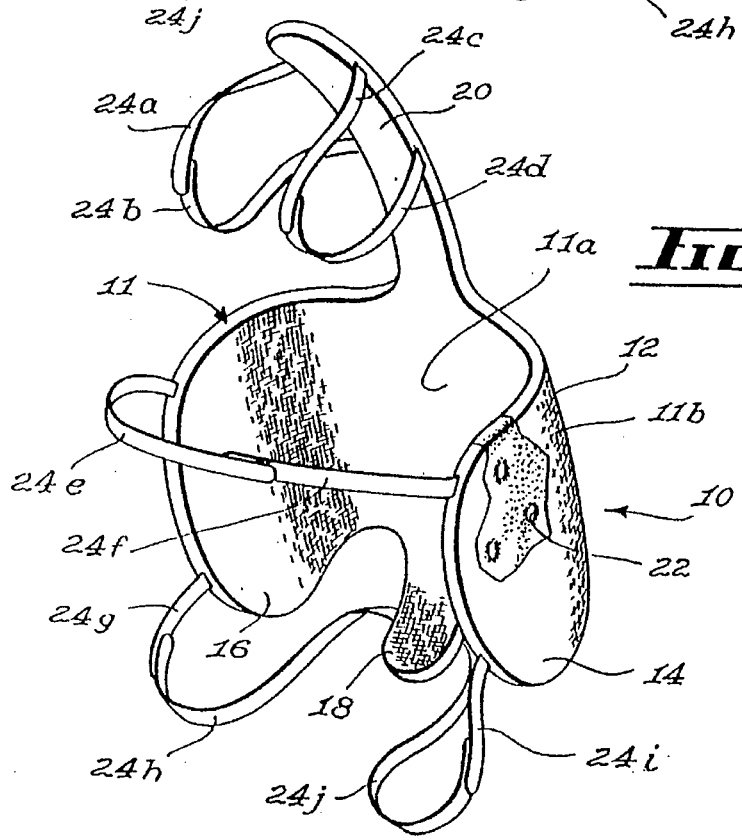

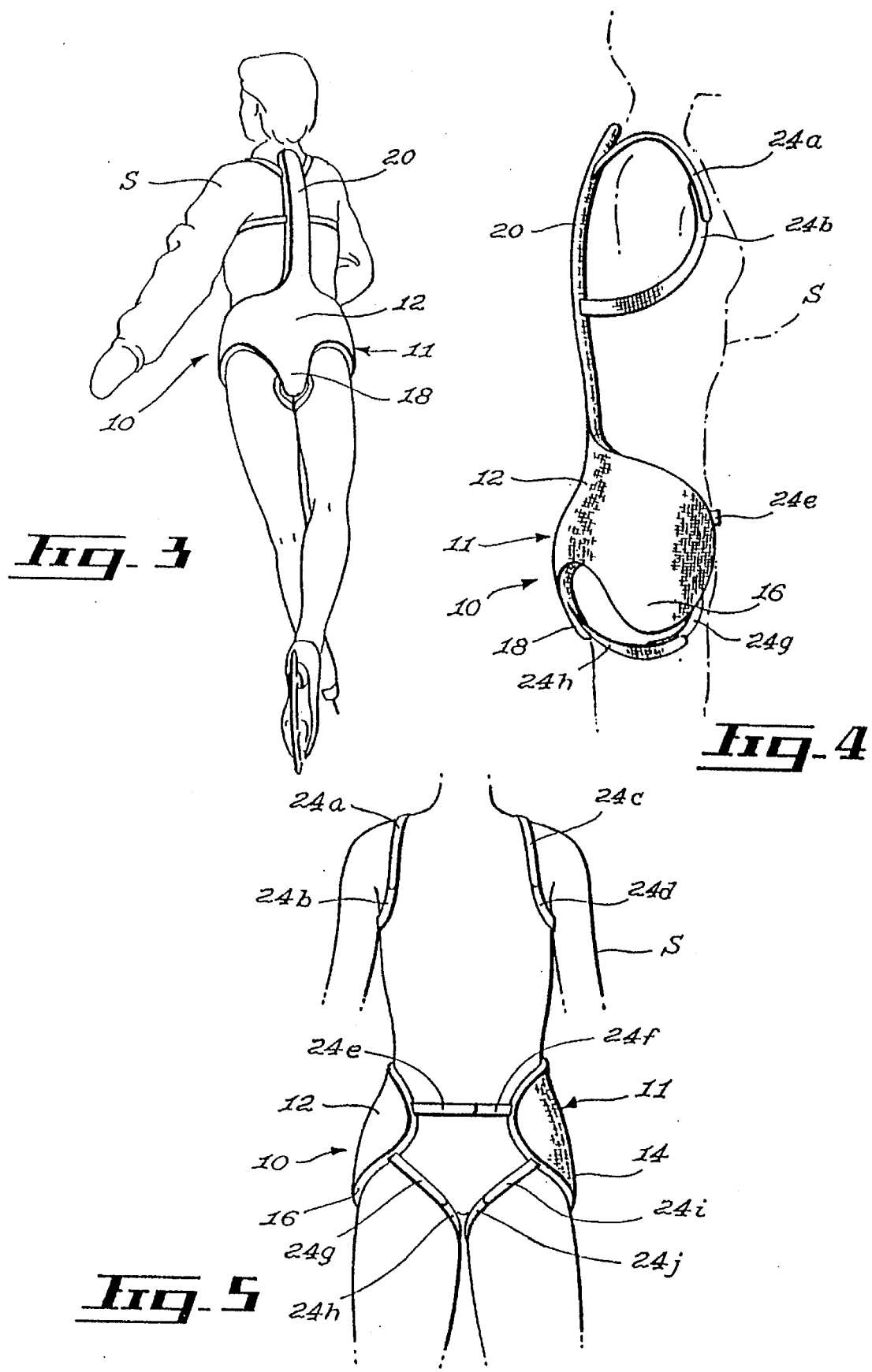

PROTECTIVE BRACE FOR FIGURE SKATERS

FIELD OF THE INVENTION

The present invention relates to a protective brace for use by figure skaters to prevent impact borne bone bruising resulting from one or more falls on the ice.

BACKGROUND OF THE INVENTION

Many sports result in impacting body contact with a hard surface. In figure skating, for example, the athletes are prone to fall against the ice. The repeatedness of the contacts with the hard ice surface can become very painful for the figure skater. Bruises often result from these falls and they become more and more painful after each fall. A critical problem is that the pain from the bruises can eventually compromise the willingness of the figure skater to perform to the limit of his or her ability. This is especially true during training sessions, when the athletes may have to skate during many consecutive hours.

The bruises often occur on the upper part of the thighs, near the protruding heads of the hip bones, when the skater falls on his side, and in the coccygeal area when the skater falls on its buttocks. The spinal area is another area where bruises often occur, being very fragile.

It is known in the art to provide protective garments for use in sporting activities to prevent bruising resulting from a fall on a hard surface.

U.S. Pat. No. 4,151,613 issued in 1979 to Jhoon G. RHEE; U.S. Pat. No. 4,761,834 issued in 1988 to Joseph J. KOLB; and U.S. Pat. No. 4,807,301 issued in 1989 to Robert C. FERBER all show protective belt-like garments for at least partially covering the hip area. Unfortunately, the RHEE and FERBER patented protective garments both cover an important part of the buttocks of the user and the hip articulation and would therefore be inappropriate for figure skaters in that these garments would hamper significantly the precise and elegant movements of a figure skater. The KOLB patent only includes small hip protectors that partially cover the hip bone heads and do not cover the coccygeal area. These three prior art devices therefore confer a limited protection due to the small body area covered by the padding. Moreover, the RHEE and FERBER patents would be very cumbersome for figure skaters due to the fabric section thereof covering the hip articulation.

Canadian patent no 1,321,855 issued in 1993 to Howard W. FISHER shows a spinal protective pad which does not laterally extend over the hip area.

Canadian patent no 1,046,201 issued in 1979 to Alfred LOBO; Canadian patent no 1,131,852 issued in 1982 to James CROTEAU; U.S. Pat. No. 4,680,812 issued in 1987 to Adolf WEIGL; and U.S. Pat. No. 5,052,052 issued in 1991 to Katheleen GILFORD, all show protective suits to be worn over the whole torso and a part of the arms and legs of the user. In each case, the padding is positioned on the suit at different places. Such suits would hamper very significantly the movements of a figure skater because it would restrain the movements of the skater articulations, particularly the hip and shoulder articulations, and the bending of the torso of the skater. This is a result of the fabric and the padding covering the upper part of the skater's body, i.e. the thighs, hips, torso, shoulders and upper arms.

U.S. Pat. No. 4,993,076 issued in 1991 to Edward G. DIERICKX shows a chest protector comprising a plurality of openings for allowing air circulation and a better flexibility of the protector.

All these garments therefore provide only partial local protection or protection over larger body areas but with significant hampering of the body movements.

OBJECTS OF THE INVENTION

It is an object of this invention to provide a protective brace for figure skaters that would effectively shield all of the the sacral, coccygeal and spinal areas while hampering as little as possible the movements of the skater's body.

It is another object of the invention that the protective brace be of the lowest manufacturing cost.

SUMMARY OF THE INVENTION

The present invention is a protective brace for use by a figure skater, said brace defining a flexible resilient shell comprising a main sheet web with transverse oppositely-extending first and second tongues integrally attached to said web, said web being destined for engagement with the lombo-sacral area of the back of said skater and to shieldingly cover the protruding hip bone heads of said skater, said first tongue sized to straddle downwardly over the coccygial section of the spine, said second tongue longer than said first tongue and sized to extend upwardly over all the lombo-thoracic section of the spine; said brace further defining removable attachment means for adjustably attaching said shell conformingly to the corresponding body parts of said skater, wherein figure skating body motions of the figure skater are not significantly hampered by the attached said brace, while thigh and spine body parts are well protected by the resilient shell.

Preferably, attachment means include straps integral to spaced portions of said web and removably attachable on the shoulders and the upper parts of the legs of said skater and around its abdomen by hook and loop fastening bands.

Advantageously, said brace shell has a plurality of spaced through-bores, said through-bores improving the flexibility of said web and said tongues.

Preferably, the material of the brace is a resilient foam plastic.

Advantageously, said web defines an edge portion adjacent said first tongue, said edge portion having opposite bulges projecting on opposite sides of said first tongue spacedly therefrom, said bulges for extending downwardly over the thighs of said skater.

DESCRIPTION OF THE DRAWINGS

In the annexed drawings:

FIG. 1 is an elevation of the exterior side of the protective brace of the invention in its unbiased, flat shape;

FIG. 2 is a perspective view of the protective brace of the invention, shown curved as it would be shaped to conformingly fit a figure skater;

FIG. 3 is an elevational view of the back of a figure skater wearing the protective brace of the invention;

FIG. 4 is a side elevation of the brace as worn by a skater, the skater being illustrated in phantom lines; and FIG. 5 is a partial front elevation of a person wearing the protective brace of the invention.

DETAILED DESCRIPTION OF THE EMBODIMENTS

FIG. 1 shows a protective brace 10 to be worn by an athlete which is prone to accidently hit hard surfaces, for example a figure skater prone to accidently fall against the ice. The protective brace 10 has a shell or insert 11 which, in an unfolded, flat shape as in FIG. 1, defines a front and a rear flat surface 11a and 11b. Shell 11 comprises a main, roughly rectangular web 12 defining a longitudinal axis and having two downwardly projecting, wide, curved extensions 14 and 16 at the respective extremities of said longitudinal axis. Shell 11 further comprises a short lower tongue 18 and a longer, upper integral elongated tongue 20, both at the mid portion, tongues 18 and 20 orthogonally extending respectively downwardly and upwardly from web 12.

The material composing shell 11 of brace 10 is flexible and resilient, so has to offer protection against shocks and permitting shell 11 to conformingly fit the wearer's body by bending to correspond to the shape of his hips and back. For example, the material of shell 11 could be a plastic such as polyurethane foam. Shell 11, as shown in FIG. 2, is therefore thin enough to be uncumbersome and to allow it the flexibility of being applied against the hips of the skater, while it must remain thick enough to properly dampen the impacts of the falls of the skater.

FIGS. 1 and 2 show that shell 11 has a plurality of spaced through-bores 22 on its surface. Through-bores 22 improve the flexibility of shell 11 for a given shell thickness thereof. This is desirable, because a greater shell thickness allows brace 10 to accomodate a wider range of falling patterns, and the fall is thus less painful for the skater (though the brace must remain thin enough to be uncumbersome, as it was already stated). Also, since the flexibility of brace 10 is enhanced with these holes 22, a better freedom of movement is thus confered to the athlete wearing brace 10.

Brace 10 is also provided with adjustable attachment means, such as a number of straps 24, usually ten straps 24a to 24j, removably and adjustably installed to web 12 and tongues 18, 20 respectively at their first extremity and freely extending through complementary elongated slots 26 made in envelope 10. Straps 24 comprise fixing means at their second free extremity, such as pairs of complementary hook and loop fastener bands 28.

To fit each skater, each shell 11 is preferably previously molded to the particular size and shape of that skater: the shells 11 are thus molded individually for each skater. Once a shell 11 is molded and the straps 24 are installed thereon, a protective brace envelope 10 is completed and has the shape shown in FIG. 2: the extremities of web 12 of shell 11 are naturally postero-anteriorly oriented and tongues 18 and 20 are slightly forwardly bent in the same direction. Since shell 11 has been molded to fit the skater, the previously stated shape of shell 11 will correspond to the shape of the hips and back of that skater.

FIGS. 3 to 5 show how brace 10 is destined to be worn. Front surface 11a of web 12 is to bear on the lombo-sacral area of the back of skater S with the extremities of the longitudinal axis folded around the thighs of the skater and the curved extensions 14 and 16 extending downwardly along the thighs. Lower tongue 18 rests on the sacral area, extending onto the coccyx, straddling the anal area. Upper tongue 20 is sized to be positioned over the lombo-thoracic section of the spine. As shown in FIGS. 2 and 5, straps 24 are removably attached together in pairs: strap 24a to 24b, and 24c to 24d, around the shoulders; straps 24e to 24f, near the lower abdomen; straps 24g to 24h, and 24i to 24j, around the upper parts of the legs. Straps 24a to 24d therefore positively secure upper tongue 20 flatly along the spine, while straps 24e to 24j hold web 12 around the tighs and the hips of the skater.

Because shell 11 of brace 10 is previously molded to fit a particular skater, to adjust brace 10 on that skater, straps 24 need only be tightened to steadfastly hold brace 10 against the body of the skater.

Brace 10 thus shields the hip bone heads, the coccyx and the spine of the skater. If he (or she) falls during his skating sessions on his hips, on his buttocks or on his back, he will instead hit the ice with brace 10 which will distribute the force of the impact through the resilient brace foamy material, and the fall will therefore be much less painful for the skater. Indeed, although brace 10 does not cover the whole back of the skater, it covers the most prominent parts of the back on which the skater is prone to fall if he is not able to interpose his hands.

Furthermore, and most importantly, the skater is allowed a relatively good freedom of movement, because brace 10 does not surround completely any body articulation (such as the thighs or the shoulders). Indeed, the brace shell 11 rests on the upper thighs, on the hip bone heads, on the lower back in the lombo-sacral area and on the spine, but only very uncumbersome, thin and light straps surround the articulations to hold brace 10. Thus, the (relatively thick) shell 11 of brace 10 does not rest on—or surround—any articulation, and consequently does not hamper the precise movements of the figure skater. Also, plastic shell 11 is quite light and its load does not weigh significantly on the skater's back.

Brace 10 can also comprise a water proof envelope (not shown), enclosing shell 11 in a substantially water-tight fashion.

It is understood that although it is stated that the brace is to be used by a figure skater, sportsmen going in for other activities such as hockey, football and the like sports would benefit from the brace within the scope of the invention.

We claim:

1. A protective brace for use by a figure skater, the skater having a back and hips, ribs and spinal column defining an upper lombo-thoracic section, a lower lombo-sacral section and a coccygial section at its lower end, the skater further having ilia on opposite sides of the spine lower area to which are connected the femur heads, each femur defining a greater trochanter laterally offset away from its respective ilium, said brace defining a soft flexible, compressible insert comprising an elongated main sheet web with oppositely-extending first and second tongues integrally and transversely attached to said web, said web being destined for engagement with the back of the skater in a perpendicular fashion relative to the spinal column at the lombo-sacral section thereof and to laterally extend and curve around the hips to shieldingly cover the protruding ilia, greater trochanters and femur heads of the skater while extending well under the skater's ribs, said first tongue sized to straddle downwardly over the coccygial section of the spinal column, said second tongue longer than said first tongue and sized to extend upwardly over all the lombo-thoracic section of the spinal column; said brace further defining removable attachment means for adjustably attaching said insert conformingly to the skater, wherein figure skating body motions of the figure skater are not significantly hampered by the attached said brace, while thigh and spinal column body parts are well protected by the soft flexible insert.

2. A protective brace as defined in claim 1, wherein the skater further defines shoulders, an abdomen and legs having upper parts, said attachment means including straps integral to spaced portions of said web and said first and second tongues and removably attachable on the shoulders and the upper parts of the legs of the skater and around its abdomen by hook and loop fastening bands.

3. A protective brace as defined in claim 1, wherein said brace insert has a plurality of spaced through-bores.

4. A protective brace as defined in claim 1, wherein the material of said insert is a resilient foam plastic.

5. A protective brace as defined in claim 1, wherein said web defines an edge portion adjacent said first tongue, originating therefrom and extending on opposite sides thereof, said edge portion having bulges downwardly projecting on the opposite sides of said first tongue spacedly therefrom, said bulges for extending downwardly over the thighs of said skater.

6. A protective brace for use by a figure skater, said brace including a main panel body, defining top and bottom long edge portions and first and second short opposite lateral edge portions, and first and second attachment members, carried respectively by said first and second lateral edge portions of said main panel body;

wherein said main panel body is made from a soft, flexible cushioning material adapted to compressingly absorb impact loads but to resiliently return to its original uncompressed state upon the impact load having been dissipated;

said main body being sized for conformingly surrounding the pelvic area of the figure skater to substantially shield the bony parts of the pelvic bones and femur heads from impact injury, said first and second attachment members for releasably looping said brace around the figure skater waist and thighs, respectively, and for biasing said flexible main panel body conformingly against the figure skater pelvic area.

7. A protective brace as in claim 6, wherein said cushioning main panel body further includes a soft cushioning elongated spine extension tongue, projecting transversely from said top edge portion of said main panel body, said tongue sized to fit over and to shieldingly cover the spine of the figure skater; and further including third and fourth attachment members, projecting from laterally opposite sides of said spine extension tongue, for releasably looping said spine extension tongue around the torso of the figure skater and for biasing said spine extension tongue flatly against the figure skater spine.

8. A protective brace as in claim 6, wherein said cushioning main panel body further includes a soft cushioning short coccygial extension tongue, projecting transversely from said bottom edge portion of said main panel body, said coccygial tongue sized to fit over and to shieldingly cover the coccyx of the figure skater; and further including one and another attachment members, projecting from laterally opposite sides of said coccygial tongue, for releasably surrounding the legs of the figure skater and for biasing said coccygial extension tongue flatly against the figure skater coccyx.

9. A protective brace as in claim 7, wherein said cushioning main panel body further includes a soft cushioning short coccygial extension tongue, projecting transversely from said bottom edge portion of said main panel body, said coccygial tongue sized to fit over and to shieldingly cover the coccyx of the figure skater; and further including one and another attachment members, projecting from laterally opposite sides of said coccygial tongue, for releasably surrounding the legs of the figure skater and for biasing said coccygial extension tongue flatly against the figure skater coccyx.

10. A protective brace as in claim 9, wherein said main panel body, including said spine extension tongue and said coccygial extension tongue, includes a plurality of flexibility-enhancing bores for improving comfort from wear of said brace by the figure skater; and all said attachment members are made from a stretchable material for adjustable body fit.

* * * * *